United States Patent
Quigley (10) Patent No.: US 8,025,693 B2
(45) Date of Patent: Sep. 27, 2011

(54) STENT-GRAFT HAVING FLEXIBLE GEOMETRIES AND METHODS OF PRODUCING THE SAME

(75) Inventor: Fergus Quigley, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 551 days.

(21) Appl. No.: 11/365,325

(22) Filed: Mar. 1, 2006

(65) Prior Publication Data

US 2007/0208421 A1     Sep. 6, 2007

(51) Int. Cl.
*A61F 2/06* (2006.01)

(52) U.S. Cl. ........................................................ 623/1.13

(58) Field of Classification Search ................ 623/1.13, 623/1.22, 1.14, 1.15, 1.16; 604/523–525
See application file for complete search history.

(56) References Cited

U.S. PATENT DOCUMENTS

| | | | |
|---|---|---|---|
| 5,026,513 A | 6/1991 | House et al. | |
| 5,282,847 A | 2/1994 | Trescony et al. | |
| 5,462,781 A | 10/1995 | Zukowski | |
| 5,466,509 A | 11/1995 | Kowligi et al. | |
| 5,628,788 A | 5/1997 | Pinchuk | |
| 5,769,884 A * | 6/1998 | Solovay | 623/1.13 |
| 5,824,036 A * | 10/1998 | Lauterjung | 623/1.11 |
| 5,843,166 A | 12/1998 | Lentz et al. | |
| 5,843,171 A * | 12/1998 | Campbell et al. | 606/198 |
| 5,876,432 A * | 3/1999 | Lau et al. | 623/1.13 |
| 5,925,061 A * | 7/1999 | Ogi et al. | 623/1.2 |
| 5,928,279 A * | 7/1999 | Shannon et al. | 623/1.13 |
| 5,961,545 A | 10/1999 | Lentz et al. | |
| 5,968,088 A * | 10/1999 | Hansen et al. | 623/1.12 |
| 6,053,943 A | 4/2000 | Edwin et al. | |
| 6,334,867 B1 * | 1/2002 | Anson | 623/1.13 |
| 6,336,937 B1 | 1/2002 | Vonesh et al. | |
| 6,361,637 B2 | 3/2002 | Martin et al. | |
| 6,398,803 B1 * | 6/2002 | Layne et al. | 623/1.13 |
| 6,524,334 B1 * | 2/2003 | Thompson | 623/1.13 |
| 6,673,103 B1 * | 1/2004 | Golds et al. | 623/1.13 |
| 6,695,875 B2 * | 2/2004 | Stelter et al. | 623/1.13 |
| 6,716,239 B2 | 4/2004 | Sowinski et al. | |
| 6,780,497 B1 | 8/2004 | Walter | |
| 6,939,371 B2 * | 9/2005 | Kugler et al. | 623/1.13 |
| 7,510,571 B2 | 3/2009 | Spiridigliozzi et al. | |

(Continued)

FOREIGN PATENT DOCUMENTS

EP     0666066     8/1995

(Continued)

*Primary Examiner* — S. Thomas Hughes
*Assistant Examiner* — Jocelin Tanner
(74) *Attorney, Agent, or Firm* — Vidas, Arrett & Steinkraus, P.A.

(57) ABSTRACT

A stent-graft or prosthesis (10) with enhanced flexibility, in particular enhanced bending flexibility, includes a radially distensible stent (24) and at least one continuously uninterrupted ePTFE tubular graft or covering (18) having a node and fibril structure. The tubular stent (24) includes opposed open ends (12', 14') and a stent wall structure (26) having opposed exterior (28) and luminal surfaces (30). The ePTFE covering (18) is securably disposed to at least one of the stent surfaces (28, 30). The ePTFE graft or covering (18) includes a tubular wall (16) that is continuously uninterrupted and desirably substantially free of slits, apertures and folds. The ePTFE graft (18) further includes a first region (20) and a second region (22), where the first region (20) has a different bending flexibility from the second region (22).

28 Claims, 8 Drawing Sheets

U.S. PATENT DOCUMENTS

| | | |
|---|---|---|
| 7,655,035 B2 * | 2/2010 | Sowinski et al. ............ 623/1.3 |
| 2002/0111667 A1 | 8/2002 | Girton et al. |
| 2003/0017775 A1 | 1/2003 | Sowinski et al. |
| 2003/0139806 A1 | 7/2003 | Haverkost et al. |
| 2004/0024442 A1 | 2/2004 | Sowinski et al. |
| 2004/0049264 A1 | 3/2004 | Sowinski et al. |
| 2004/0157024 A1 | 8/2004 | Colone |
| 2004/0193140 A1 * | 9/2004 | Griffin et al. ............ 604/524 |
| 2004/0236402 A1 | 11/2004 | Layne et al. |
| 2005/0240261 A1 | 10/2005 | Rakos et al. |
| 2006/0058867 A1 | 3/2006 | Thistle et al. |
| 2006/0149361 A1 | 7/2006 | Henderson |
| 2006/0178723 A1 | 8/2006 | Lentz et al. |
| 2009/0048657 A1 | 2/2009 | Duran et al. |

FOREIGN PATENT DOCUMENTS

| | | |
|---|---|---|
| WO | 87/05796 | 10/1987 |
| WO | 94/19029 | 9/1994 |
| WO | WO 00/45741 | 8/2000 |
| WO | WO 2006/073974 | 7/2006 |

* cited by examiner

STENT-GRAFT HAVING FLEXIBLE GEOMETRIES AND METHODS OF PRODUCING THE SAME

FIELD OF THE INVENTION

The present invention relates to flexible stent-graft devices and methods for making the same. More particularly, the present invention relates to a radially distensible stent and a non-textile polymeric tubular structure having a plurality of graft regions that differentially bend or plastically deform upon application of a bending stress.

BACKGROUND OF THE INVENTION

An intraluminal prosthesis is a medical device used in the treatment of diseased bodily lumens. One type of intraluminal prosthesis used in the repair and/or treatment of diseases in various body vessels is a stent. A stent is generally a longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminal vascular stents, have included helically wound coils which may have undulations or zig-zags therein, slotted stents, ring stents, braided stents and open mesh wire stents, to name a few. Super-elastic materials and metallic shape memory materials have also been used to form stents.

A graft is another commonly known type of intraluminal prosthesis which is used to repair and replace various body vessels. A graft provides a lumen through which fluids, such as blood, may flow. Moreover, a graft is often configured as being generally impermeable to blood to inhibit substantial leakage of blood therethrough. Grafts are typically hollow tubular devices that may be formed of a variety of materials, including textile and non-textile materials.

A stent and a graft may be combined into a stent-graft endoprosthesis to combine the features and advantages of each. For example, tubular coverings have been provided on the inner and/or outer surfaces of stents to form stent-grafts. It is often desirable to use a thin-walled graft or covering in the stent-graft endoprosthesis to minimize the profile of the endoprosthesis and to maximize the flow of blood through the endoprosthesis. In such cases, non-textile materials, such as polymeric tubes or sheets formed into tubes, are often used. Expanded polytetrafluoroethylene or e-PTFE is one common polymeric material used as the graft portion of a stent-graft endoprosthesis. Expanded polytetrafluoroethylene grafts, however, are subject to plastic deformation, especially when, for example, compressing the stent-graft for loading into its delivery system, delivering the stent-graft through a highly tortuous bodily lumen and/or placing or deploying the stent-graft at the target implant site. Such plastic deformation may lead to the tearing of the ePTFE, leaving the stent-graft endoprosthesis prone to leakage of blood therethrough. Furthermore, plastic deformation of expanded polytetrafluoroethylene grafts may lead to physical deformities in the graft, such as buckling, which is also undesirable because it may lead to poor blood flow patterns.

Sheets or films of ePTFE have been used to cover or line stents. For example, U.S. Pat. Nos. 5,700,285 and 5,735,892 to Myers et al. describe overlapping a sheet of ePTFE onto a stent to form a tubular graft. The graft is secured to the stent by an application of thermoplastic adhesive and heat treatment to melt the adhesive. A seam, which is formed where the sheet overlaps, is also sealed through the use of the thermoplastic adhesive. Such stent-grafts having a unitary tubular ePTFE covering adhesively secured to the stent, however, do not have differential flexibility associated with the graft to augment bending or plastic deformation of the graft when subjected to certain stresses, such as bending stresses during delivery through tortuous bodily lumens.

U.S. Pat. No. 6,361,637 to Martin et al. described the securement or interweaving of ePTFE graft strips through helical windings of an undulating stent wire. The ePTFE strips are spaced apart from the apices of the undulating wire such that no strip completely covers a winding of the undulating wire. The graft strips are secured to the stent wire by use of a thermoplastic adhesive and the application of heat. While such a resulting stent-graft may have additional flexibility as compared to the above-described stent-grafts to Myers et al., the graft wall is non-continuous, thereby not providing by itself a fluid tight graft wall.

Apertures have also been imparted into the walls of tubular ePTFE grafts to increase flexibility. For example, U.S. Pat. No. 6,673,103 to Golds et al. describes a composite stent-graft tubular prosthesis which includes an inner PTFE tubular structure, an outer PTFE tubular structure positioned about the inner PTFE tubular structure and a diametrically deformable stent interposed between the inner and outer PTFE tubular structures. Portions of the stent are exposed exteriorly via apertures in the outer PTFE structure to render the composite prosthesis longitudinally flexible. Moreover, U.S. Pat. No. 6,398,803 to Layne et al. described partially encapsulated stents which are made by using gaps or slits cut into ePTFE covering material. By selecting the size and position of the apertures or slits in the ePTFE covering, the '803 patent describes that it is possible to leave certain parts of the stent unencapsulated to facilitate flexibility and expansion of the device. While such stent-grafts may have additional flexibility as compared to the above-described stent-grafts to Myers et al., the graft walls are not continuous, thereby not providing by itself a fluid tight graft wall U.S. Pat. No. 6,344,054 to Parodi describes a stent graft having its graft being secured to only one end of the stent. Such a graft avoids undue stresses being placed on the graft during contraction and expansion of the stent by only securing one end of the graft to the stent.

U.S. Patent Application Publication No. 2003/0220682 to Kujawski describes a hybrid braided stent having a plurality of overlapping graft segments. The graft segments are described as being textile graft segments made by, for example, braiding yarns. One end of a graft segment is secured to the stent, and the other end of the graft segment overlaps an adjacent secured graft segment.

ePTFE surfaces have been modified to alter porosity. For example, U.S. Pat. No. 5,466,509 to Kowligi et al. described a more porous ePTFE which is obtained by impressing a pattern into extruded PTFE and then expanding the PTFE.

The pattern is described as being impressed by knurling or rolling a sheet of PTFE sheet between rollers having a pattern formed on the surface of the roller. A roller with a coarse pattern is described as producing a wider distribution of internodal distances of the ePTFE as compared to a finer pattern, thereby increasing the porosity of the ePTFE material.

U.S. Pat. No. 5,462,781 to Zukowski describes an implantable porous expanded polytetrafluoroethylene material having a microstructure of nodes interconnected by fibrils where its surface has been modified by the removal of fibrils so that under magnification the surface has the appearance of freestanding node portions not interconnected by fibrils but rather having open valleys disposed between the freestanding node portions. Unmodified material beneath the surface is described as maintaining the original microstructure of nodes interconnected by fibrils. The modification is described as bone done by exposing the surface to radio frequency gas plasma discharge with a reactive etching gas. The modified surface is described as having increased hydrophobicity. Such a modified surface is described as having improved blood contact properties and tissue ingrowth characteristics useful as an implantable device, such as a breast prosthesis.

U.S. Pat. No. 6,780,497 to Walter describes a process for surface treating ePTFE. The described process employs a laser to surface-modify an ePTFE structure to create a macro-roughened surface that has is described as being highly porous and modified to be highly textured or having increased roughness to promote tissue ingrowth.

While these later patents describe surface modification or ePTFE to increase porosity or surface modification to increase tissue ingrowth characteristics, these patents fail to describe modification of ePTFE to improve bending characteristics or to improve flexibility of the ePTFE material as compared to untreated ePTFE.

Thus, there is a need for a stent-graft having a polymeric graft, including an ePTFE graft that has enhanced flexibility.

SUMMARY OF THE INVENTION

In one aspect of the present invention, prosthesis or stent-graft with enhanced flexibility, in particular enhanced bending flexibility is provided. The stent-graft includes a radially distensible, tubular stent having opposed open ends and a stent wall structure having opposed exterior and luminal surfaces; and a continuously uninterrupted ePTFE tubular graft having a node and fibril structure securably disposed to at least one of the stent surfaces. For the purposes of this invention, the terms tubular graft and tubular covering may be used interchangeably. The graft desirably comprises a tubular wall substantially free of slits, apertures and folds. The graft may further include a first region and a second region, the first region having a different bending flexibility from the second region.

Desirably, the stent used in the devices of the present invention may include a longitudinal length, wherein the longitudinal length remains substantially constant upon radial expansion or radial contraction of the stent. The stent may be a self-expanding stent, a balloon-expandable stent or combinations thereof. The stent may be made from a biocompatible material, such as a metallic material, a polymeric material, a bioabsorbable material, a biodegradable material, and combinations thereof. Desirably, the stent may include a plurality of undulating stent segments. For example, the stent may include an undulating wire helically wound into a plurality of circumferential adjacent windings to define the stent wall structure.

The first region of the ePTFE graft may be securably attached to at least one of the circumferential windings of the undulating wire on at least one of the stent surfaces. The second region of the ePTFE graft may be disposed between at least two adjacent windings of the circumferential windings of the undulating wire. Desirably, the second region has a greater bending flexibility that the first region.

In one aspect of the present invention, the second region of the graft may include at least one circumferential recess. Further, the first region of the graft is free of circumferential recesses. Desirably, the second region preferentially deforms when subjected to a bending stress as compared to the first region.

In another aspect of the present invention, the node and fibril structure of the first ePTFE region is different from the node and fibril structure of the second region ePTFE. Desirably, the fibril structure at the first region is more circumferentially orientated than the fibril structure at the second region. The fibril structure at the first region may be formed by axially stretching the first region by a first amount and the fibril structure at the second region may be formed by axially stretching the second region by a second amount. Typically, the first amount of axial stretching is greater than the second amount of axial stretching. For example, the first amount of axial stretching may be from about 1,000% to about 2,000% and the second amount of axial stretching may be from about 200% to about 800%. Desirably, the second region preferentially deforms when subjected to a bending stress as compared to the first region.

The stent-graft of the present invention may further include a second ePTFE tubular graft securably disposed to the other of one the stent surfaces.

In another aspect of the present invention, an implantable prosthesis with enhanced flexibility is provided. The prosthesis may include a continuous uninterrupted, and desirably seamless, non-textile polymeric tubular graft. The tubular graft generally has a substantially smooth tubular wall. In some embodiments, the graft may be substantially free of slits and apertures and includes a first region and a second region, wherein the first region has a different bending flexibility than the second region. Desirably, the first region has a different plastic deformation rate than the second region.

The graft may be made from polymeric graft material, such as a polyester, a polypropylene, a polyethylene, a polyurethane, a polynaphthalene, an expanded polytetrafluoroethylene, a silicone, and combinations and copolymers thereof.

Desirably, the graft is made from expanded polytetrafluoroethylene. The ePTFE graft comprises a node and fibril structure, and the node and fibril structure of the first region may be different from the node and fibril structure of the second region. Desirably, the fibril structure at the first region is more circumferentially orientated than the fibril structure at the second region. The fibril structure at the first region may be formed by axially stretching the first region by a first amount, and the fibril structure at the second region was formed by axially stretching the second region by a second amount. Desirably, the first amount of axial stretching is greater than the second amount axial stretching. For example, the first amount of axial stretching may be from about 1,000% to about 2,000%, and the second amount of axial stretching may be from about 200% to about 800%. Desirably, the second region preferentially deforms when subjected to a bending stress as compared to the first region.

The prosthesis of this aspect of the present invention may further include a radially distensible, tubular stent. Desirably, the stent includes a plurality of undulating stent segments, for example an undulating wire helically wound into a plurality of circumferential windings to define a stent wall structure. The first region of the ePTFE graft may be securably attached to at least one of the circumferential windings of the undulating wire. The second region of the ePTFE graft is disposed between at least two adjacent windings of the circumferential windings of the undulating wire. Desirably, the substantially smooth tubular wall is free of folds, crimps and pleats.

In another aspect of the present invention, a method of making a stent-graft having increased bending flexibility is provided. The method of this aspect of the present invention includes the steps of providing a radially distensible, tubular stent including opposed open ends and a stent wall structure having opposed exterior and luminal surfaces; providing a continuously uninterrupted and optionally seamless ePTFE tubular graft having a node and fibril structure securably disposed to at least one of the stent surfaces, the graft including a tubular wall substantially free of slits, apertures and folds, the graft further including a first region and a second region; and providing the first region with a different bending flexibility from the second region. Desirably, the step of providing the first region with a different bending flexibility from the second region may further include providing at least one circumferential recess at the second region of the graft, wherein the first region of the graft is free of circumferential recesses. Alternatively, or in addition to, the step of providing the first region with a different bending flexibility from the second region may further include axially stretching the first region by a first amount; and axially stretching the second region by a second amount, wherein the first amount and second amounts are different. In some embodiments, the first amount may be greater than the second amount. The first amount of axial stretching may be from about 1,000% to about 2,000%, and the second amount of axial stretching may be from about 200% to about 800%.

DETAILED DESCRIPTION OF THE PREFERRED EMBODIMENT

Figure 1:
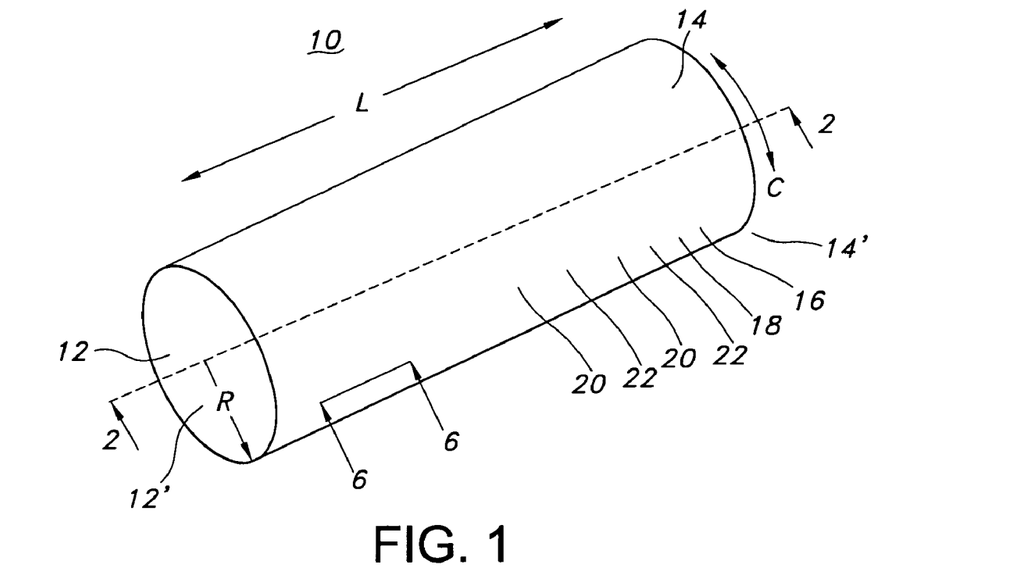
FIG. 1 is a perspective view of a stent-graft having increased bending flexibility according to the present invention.
Figure 2:
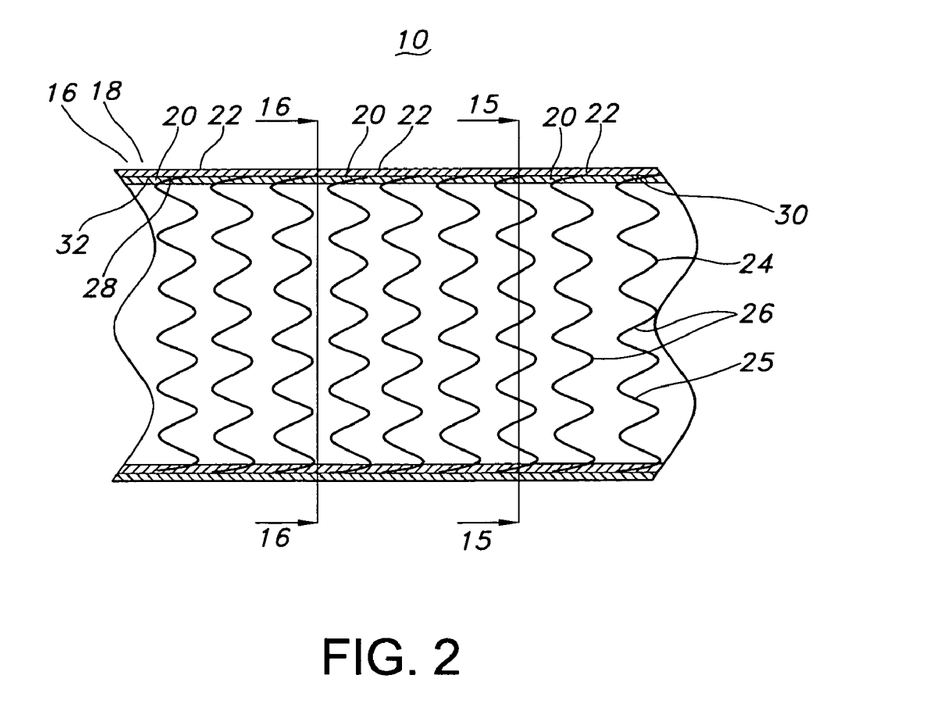
FIG. 2 is an expanded, partial cross-sectional view of the stent-graft of FIG. 1 taken along the 2-2 axis.

FIG. 1 is a perspective view of a stent-graft 10 having enhanced flexibility of the present invention. The stent-graft 10 is a hollow, tubular structure or device having opposed open ends 12, 14. The stent-graft 10 includes a tubular wall 16 disposed between the open ends 12, 14. As depicted in FIG. 1, the tubular wall 16 extends along the longitudinal direction, which is depicted as the L-axis, of the stent-graft 10. The tubular wall 16 includes a graft 18 having plurality graft portions or regions 20, 22 that, as described below, have varied or different flexibilities, such as bending flexibilities. The graft wall 16 also extends around the circumference, which is indicated by the C-axis or C-vector, of the stent-graft 10. The R-axis defines a radial extent of the stent-graft 10 of the present invention. As depicted in FIG. 1, stent-graft 10 is a substantially longitudinally straight tubular device, but the present invention is not so limited. Stent-graft 10 may have a varying radial extent, for example, a varied diameter, outwardly or inwardly flared extents, and the like FIG. 2 is an expanded, partial cross sectional view of the stent-graft 10 of FIG. 1 taken along the 2-2 axis. As depicted in FIG. 2, the stent-graft 10 may include a stent 24. Various stent types and stent constructions may be employed in the invention as the stent 24. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. Nos. 4,503,569 to Dotter; 4,733,665 to Palmaz; 4,856,561 to Hillstead; 4,580,568 to Gianturco; 4,732,152 to Wallsten, 4,886,062 to Wiktor, and 5,876,448 to Thompson, all of whose contents are incorporated herein by reference.

Desirably, stent 24 is one that has minimal foreshortening, i.e., a stent wherein its longitudinal length remains substantially constant upon radial expansion or radial contraction of the stent. As depicted in FIG. 2, such a stent 24 having minimal foreshortening may include undulating stent portions 26. Such undulating stent portions 26 will be further described in conjunction the description of FIGS. 10-13.

Figure 3:
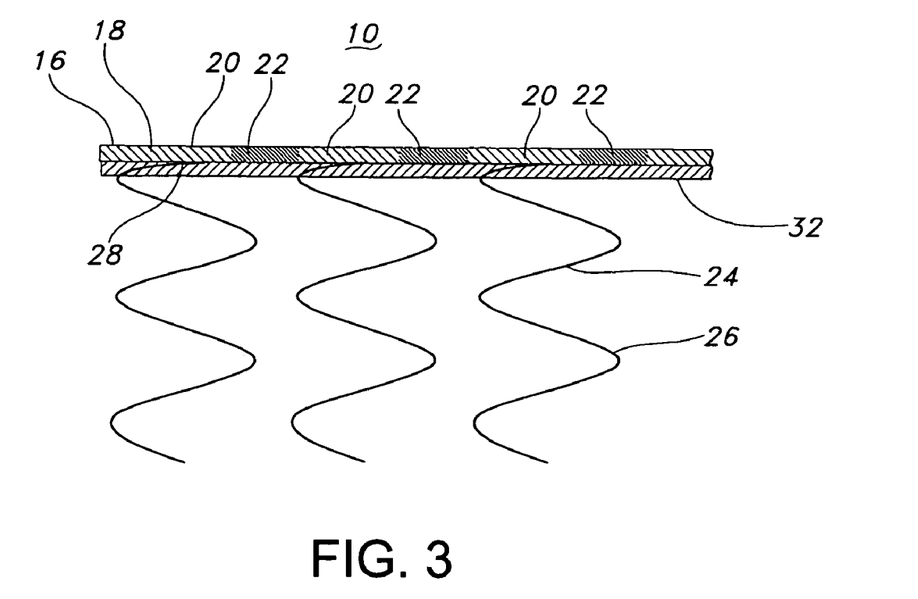
FIG. 3 is a partial exploded view of the stent-graft of FIG. 2 further detailing graft regions having different flexibilities of the present invention.

As depicted in FIGS. 2-3, the tubular wall 16 of graft 18 includes graft regions 20, 22 that have different bending flexibilities and are disposed at different locations along the stent-graft 10. For example, the graft region 20 may be securably disposed to one or more undulating stent portions 26 of the stent 24, and the second graft region 22 may not secured to the undulating stent portions 26. Although the graft regions 20, 22 are depicted as being disposed over the exterior surfaces 28 of the stent 24, the present invention is not so limited. For example, the graft regions 20, 22 may be disposed over interior or luminal surfaces 30 of the stent 24. Desirably, the graft wall 16 of graft 18 is an unfolded wall or graft, i.e., the graft is not bent or doubled up so that one part lies on another part of the same segment. Desirably, the graft wall 16 is a substantially smooth tubular wall that is free of folds, crimps, pleats and the like. Further, the graft wall 16 is desirably a substantially continuous tubular wall, i.e., one that is free of slits, openings, apertures and the like.

Figure 4:
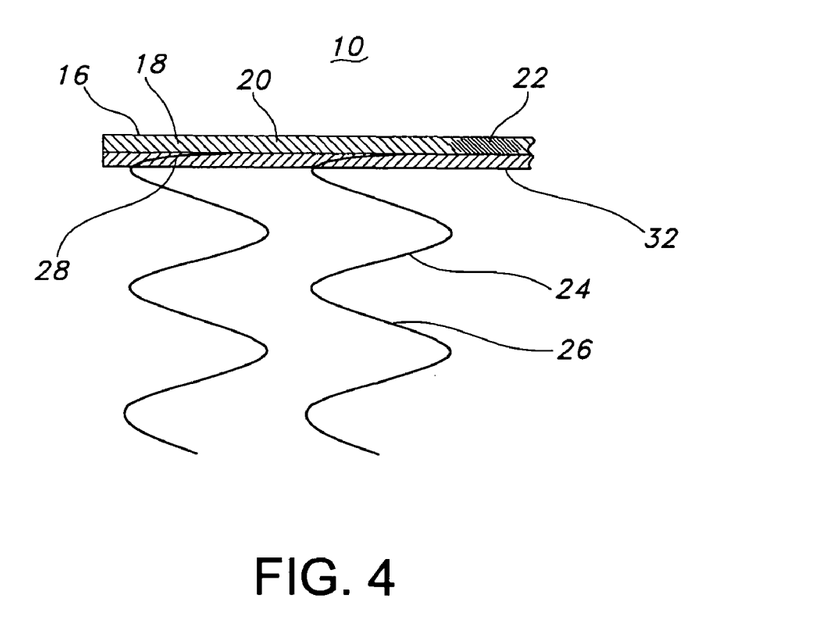
FIG. 4 is a partial exploded view of the stent-graft of FIG. 2 further detailing an alternate aspect of the graft regions having different flexibilities of the present invention.

While the first graft region 20 is depicted in FIGS. 2-3 as being secured to one undulating stent portions 26 of the stent 24, the present invention is not so limited. The first graft region 20 may suitably be secured to at least one or more of the adjacent undulating stent portions 26 of the stent 24. For example, as depicted in FIG. 4, the graft region 20 is secured to at least two of the undulating stent portions 26. Further, while the second graft region 22 is depicted as being disposed between adjacent undulating stent portions 26, the present invention is not so limited, the second graft region 22 may also be disposed over some the undulating stent portions 26. In general, the flexibility of the stent-graft 10 of the present invention may increase with an increasing number of the graft regions 20, 22. The flexibility of the stent-graft 10 of the present invention may also increase with decreasing number of undulation stent portions 26 to which the first regions 20 are secured thereto.

The stent-graft 10 of the present invention may optionally include a second tubular graft structure 32. The second tubular graft structure 32 may be a continuous tubular structure, similar or different from the graft 18 having the graft regions 20, 22.

Desirably, the stent 24 is made from any suitable implantable, biocompatible, bioabsorbable or biodegradable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like.

Further, the stent 24 may have a composite construction, such as described found in U.S. Patent Application Publication 2002/0035396 A1, the contents of which is incorporated herein by reference. For example, the stent 24 may have an inner core of tantalum gold, platinum, iridium or combination of thereof and an outer member or layer of nitinol to provide a composite wire for improved radiocapacity or visibility. Alternatively, a radiopaque member or wire may be secured to a portion of the stent 24 for improved radiocapacity or visibility.

Figure 5:
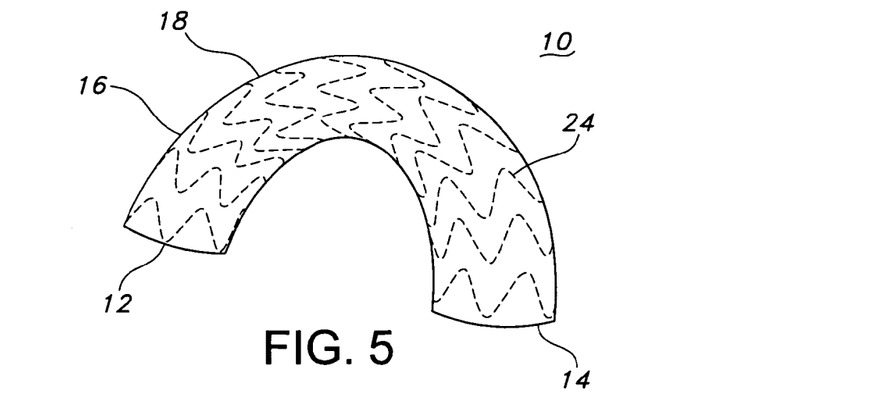
FIG. 5 is a side elevational view of the stent-graft of FIG. 2 being in a bent position.

As depicted in FIG. 5, which is a side elevational view of the stent-graft 10 of the present invention, the stent-graft 10 is capable of being highly bent or contoured without kinking of the device and without undesirable deformation of the tubular wall 16. Because of the varied bending flexibilities of the graft regions 20 and 22, these regions or portions plastically deform to conform to the curvature of the stent-graft 10. While the stent-graft 10 is depicted as having a substantially equal diameter, the present invention is not so limited. For example, the stent-graft 10 may have a varying diameter, for example, having an outwardly or inwardly flared end at either or both of its ends 12, 14. Further, while the stent-graft 10 is depicted as a single lumen device, the present invention is not so limited. For example, the stent-graft 10 may include a tubular branch or branches to define a bifurcated or multi-lumen stent-graft.

The non-textile, polymeric graft 18 and/or the second tubular graft structure 32 may suitably be made from extruded, molded or cast polymeric materials. As used herein, the term "textile" refers to a material, such as a yarn, that has been knitted, woven, braided and the like into a structure, including a hollow, tubular structure. As used herein, the term "non-textile" and its variants refer to a material formed by casting, molding or extruding techniques to the exclusion of typical textile forming techniques, such as braiding, weaving, knitting and the like. Nonlimiting examples of useful polymeric materials for the non-textile polymeric graft portions include polyesters, polypropylenes, polyethylenes, polyurethanes, polynaphthalenes, polytetrafluoroethylenes, expanded polytetrafluoroethylene, silicone, and combinations and copolymers thereof. Desirably, the polymeric material polytetrafluoroethylene (PTFE), including expanded polytetrafluoroethylene (ePTFE).

PTFE exhibits superior biocompatibility and low thrombogenicity, which makes it particularly useful as vascular graft material in the repair or replacement of blood vessels or other bodily lumens. Desirably the non-textile layer is a tubular structure manufactured from ePTFE. The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to about 2,000 percent by linear dimension, for example, from about 100 percent by linear dimension to about 2,000 percent by linear dimension, from about 100 percent by linear dimension to about 600 percent by linear dimension, from about 600 percent by linear dimension to about 2,000 percent by linear dimension, and the like. Such expansion properties are not limiting. Such physically modified ePTFE material may be made by reorienting the node and fibril structure through application a radially expansive and longitudinally foreshortening force. The physically modified ePTFE tubular structure is able to be elongated or expanded and then returned to its original state without an elastic force existing therewithin. Additional details of the physically modified ePTFE and methods for making the same can be found in U.S. Pat. No. 6,716,239, the contents of which are incorporated by reference herein.

Figure 6:
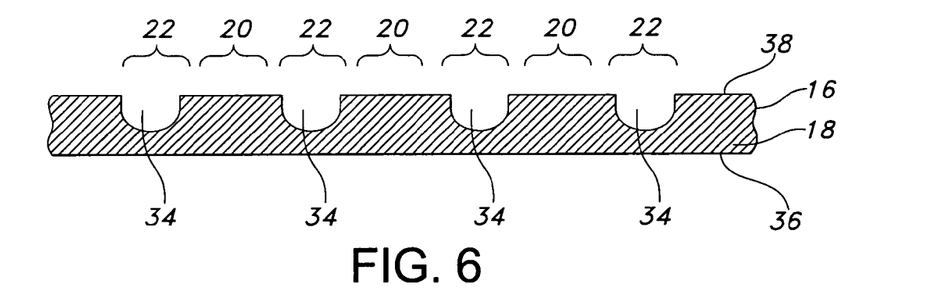
FIG. 6 is a partial cross-sectional view of graft wall of FIG. 1 taken along the 6-6 axis showing circumferential recesses for increased flexibility.

FIG. 6 is a partial side view of a portion of the tubular wall 16 of the graft 18 of FIG. 1 taken along the 6-6 axis. As depicted in FIG. 6, the second graft region 22 may include a recess 34. Desirably, recess 34 is a circumferential recess, i.e., one that extends at least substantially along the circumferential axis, C, of the stent-graft 10 of the present invention. The recess 34 may be formed into the tubular wall 16 by any suitable method, for example by laser cutting/ablation, chemical etching, electrochemical etching, and the like. The recess 34 is not a crimping of the tubular wall 16 as the luminal surface 36 of the graft wall 16 remains substantially smooth, i.e., free of folds, pleats and the like. The exterior surface 38 of the graft wall 16 also does not have protrusions typical of folds, pleats crimps, and the like. With the recess 34, the graft regions 22 will bend and/or plastically deform to a greater extent that the graft region 20, which does not contain any recesses 34. In other words, when the stent-graft 10 is placed under a bending stress, such as when being moved through tortuous bodily lumens, graft regions 22 will preferentially bend as compared to the graft regions 20.

Figure 7:
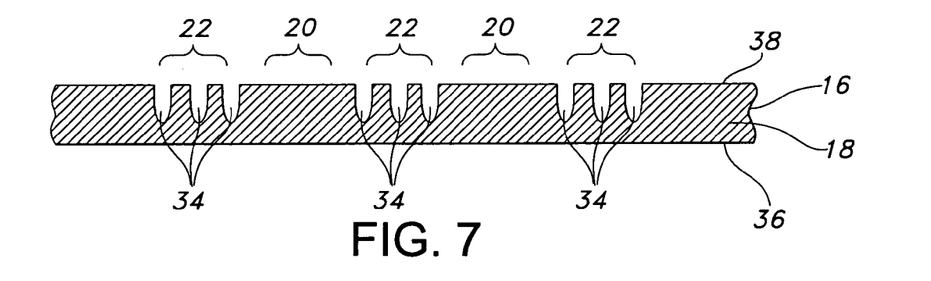
FIG. 7 is a partial cross-sectional view of graft wall of FIG. 1 taken along the 6-6 axis showing alternate circumferential recesses for increased flexibility.

The present invention, however, is not limited to graft regions 22 having a single recess 34. As depicted in FIG. 7, the graft region 22 may have a plurality of circumferential recesses 34.

Figure 8:
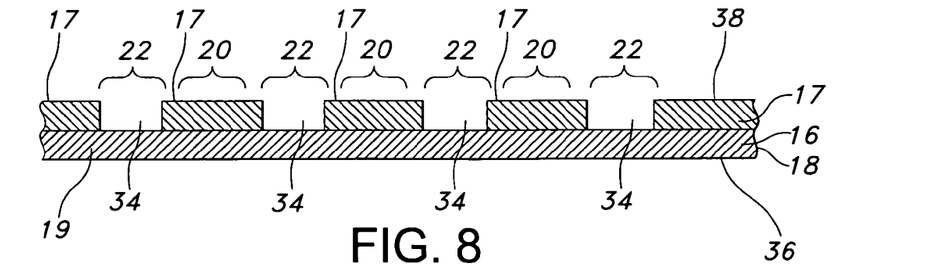
FIG. 8 is a partial cross-sectional view of graft wall of FIG. 1 taken along the 6-6 axis showing alternate circumferential recesses formed by composite overlay of ePTFE portions onto an ePTFE tube for increased flexibility.

Further, as depicted in FIG. 8, the present invention is not limited to a stent-graft 10 having a recess 34 formed laser cutting/ablation, chemical etching, electrochemical etching, and the like. Recesses 34 may be formed from a composite overlay of ePTFE elongate members or strips 17 onto a tubular ePTFE substrate 19. The strips 17 may be placed apart to define the recesses 34 therebetween. The strips 17 are securably disposed onto the substrate 19 to define the tubular wall 16 of the graft 18. Such securement includes, but is not limited to, mechanical securement, such as thermal fusion or heat bonding, chemical securement, such as adhesive bonding, or combinations thereof.

Figure 9:
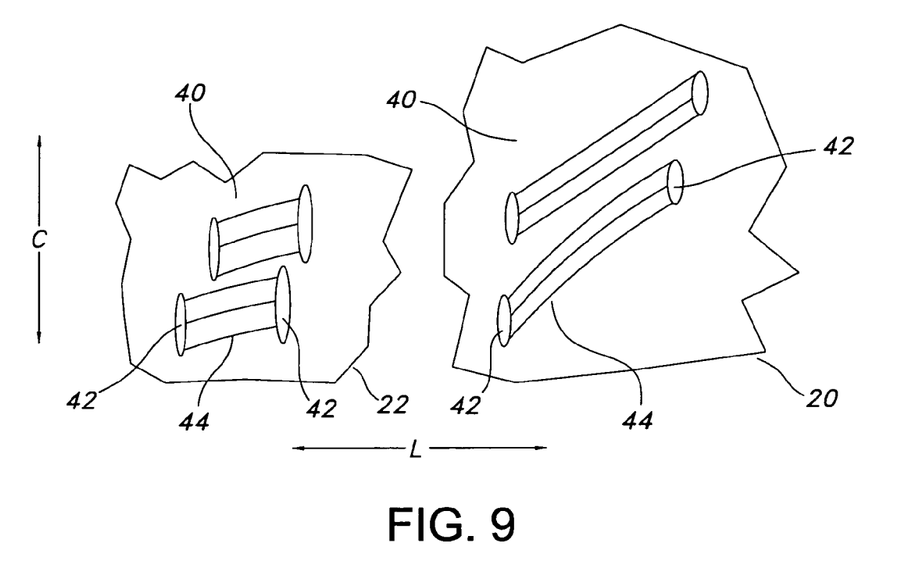
FIG. 9 is a schematic depiction of portions of the graft wall of FIG. 1 illustrating different node and fibril orientations useful for imparting flexibility to the graft of the present invention.

A portion of the node and fibril structure 40 of graft regions 20 and 22 are schematically depicted in FIG. 9. As depicted in FIG. 9, ePTFE includes a node and fibril structure 40 having nodes 42 and fibrils 44, orientated circumferentially (as indicated by the "C" vector) and axially or longitudinally (as indicated by the "L" vector), as shown. The ePTFE used of graft 18 is made by first forming a tube of polytetrafluoroethylene, desirably by extrusion of a tube which provides substantially longitudinally oriented fibrils (not shown) in the tube. Portions of the tube or graft 18 may be radially expanded and longitudinally foreshortened with or without the application of heat. The radial expansion and longitudinal foreshortening desirably is controlled to circumferentially and/or axially shift the nodes in contrast to changing the shape of the nodes or lengthening the nodes. The circumferential shift of the nodes results in a hingeable rotation of the fibrils. Additional details of such ePTFE and methods for forming the same may be found in U.S. Pat. No. 6,716,239 to Sowinski et al., the contents of which are incorporated herein by reference.

The node and fibril structure 40 of graft region 20 is circumferentially and/or axially shifted to a greater extent that the node and fibril structure 40 of the graft portion 22. In other words, the fibrils 44 of the graft region 20 are more circumferentially and/or axially oriented that the fibrils 44 of the graft region 22. Such different node and fibril structures 40 may be obtained by controlling the degree of radial expansion and longitudinally foreshortening. Desirably, the amount of axial stretching for the graft region 20 is from about 1,000% to about 3,000%, for example, from about 1,500% to about 2,500%, desirably from about 1,800% to about 2,300%, preferably from about 2,000% to about 2,100%. Desirably, the amount of axial stretching for the graft region 22 is from about 200% to about 800%, for example, from about 300% to about 700%, preferably about 400%. The graft region 20 is stiffer that the graft region 22, so that the graft region 22 will preferentially deform, draw away from the graft region 20 and experience a stress concentration, such as a bending stress concentration, to a greater extend than the graft region 20.

Figure 10:
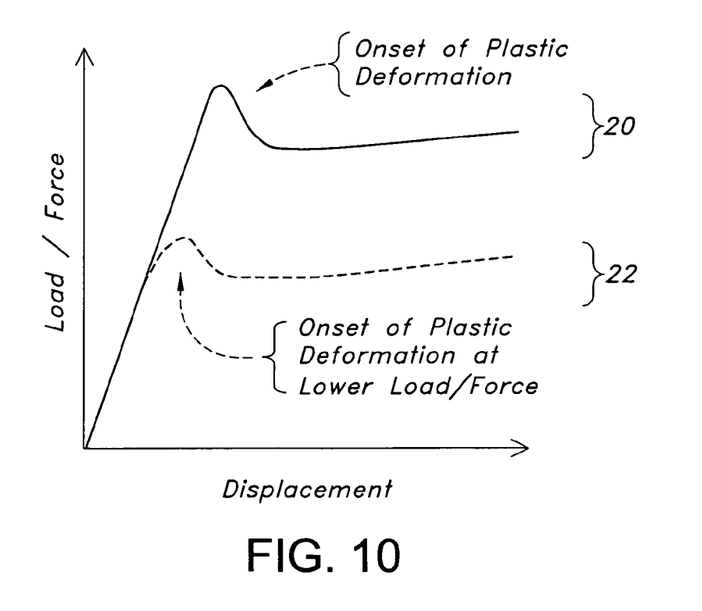
FIG. 10 is a schematic depiction of increased flexibility through plastic deformation at lower load force according to the present invention.

FIG. 10 is a schematic depiction of stress curves for the graft regions 20, 22 of the present invention: As depicted in FIG. 10, graft regions 22 plastically deform, as indicated by the onset of plastic deformation, at a lower force or load than the graft regions 20. Such lower plastic deformation may be imparted by the inclusion of the above-discussed recesses 34 in the graft region 22 and/or by altering the node and fibril structure 42 to hingeably rotate the fibrils 44 to a degree of greater circumferential orientation in the graft region 20.

Figure 11:
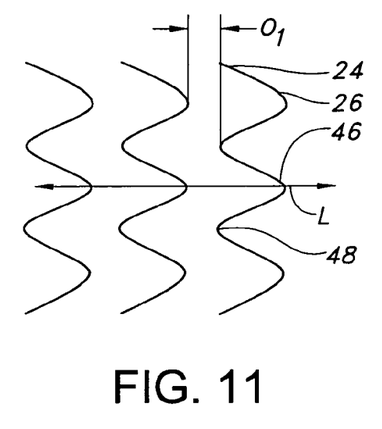
FIG. 11 is a partial exploded view of the stent of FIG. 2 further detailing the stent configuration.

FIGS. 11-14 depict further details of the undulating stent portion 26 useful with the present invention. As depicted in FIG. 11, peaks 46 of the undulating stent portions 26 may be substantially longitudinally aligned. Further, the undulating stent portions 26 may be longitudinally offset from one and the other by a length, $O_1$. For example, the peaks 46 of one undulating stent portion 26 may be longitudinally offset from the valleys 48 of an adjacent undulating stent portion 26 by a distance $O_1$. Any suitable offset length, $O_1$, may be used with the present invention. Desirably, the offset, $O_1$, is less than the longitudinal length defined by the longitudinal distance from the peak 46 and the valley 48 of the undulating stent portion 26.

Figure 12:
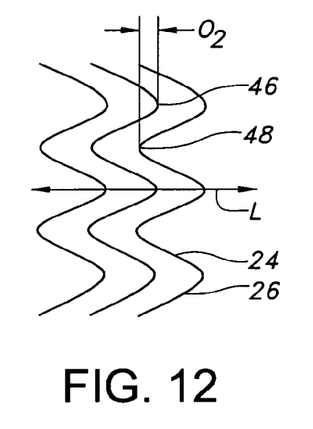
FIG. 12 is a partial exploded view of the stent of FIG. 2 further detailing an alternate stent configuration.

In another aspect, nested undulating stent portions 26 may be useful as the stent 24 of the present invention. As depicted in FIG. 12, the valleys 48 of one undulating stent portion 26 may be longitudinally disposed within a circumferential plane defined by the peaks 46 of an adjacent undulating stent portion 26, which is depicted as offset $O_2$ in FIG. 12. Desirably, the offset, $O_2$, is less than the longitudinal length defined by the longitudinal distance from a peak 46 and a valley 48 of the undulating stent portion 26.

Figure 13:
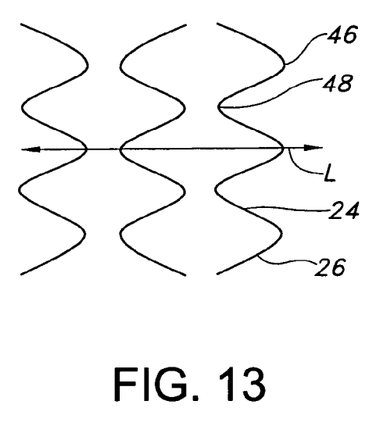
FIG. 13 is a partial exploded view of the stent of FIG. 2 further detailing yet another alternate stent configuration.
Figure 14:
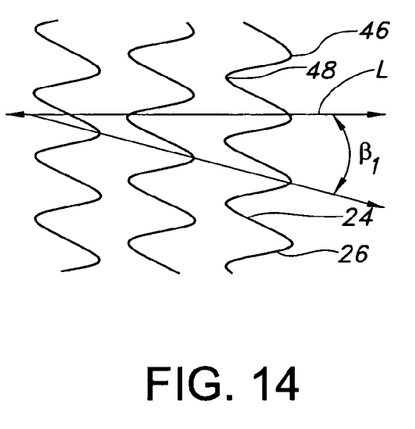
FIG. 14 is a partial exploded view of the stent of FIG. 2 further detailing yet another alternate stent configuration.

The present invention, however, is not limited to undulating stent portions 26 having longitudinally aligned peaks 46 and valleys 48 as depicted in FIGS. 11-12. For example, as depict in FIG. 13, certain peaks 46 of adjacent undulating stent portions 26 may be proximally disposed relative to one and the other in the longitudinal direction while other peaks 46 are distally disposed to one and the other. As compared to FIG. 11, the peaks 46 and valleys 48 depicted in FIG. 13 are not in substantial longitudinal phase with one and the other. Moreover, as depicted in FIG. 14, the peaks 46 of adjacent undulating stent portions 26 may be offset from the longitudinal axis by an angle, for example by a angle of $\beta_1$. The degree of angular offsetting, i.e., $\beta_1$ may be suitably varied, for example from about 1° to about 45°, and need not be constant along the longitudinal length of the stent-graft 10 of the present invention. The degree of angular offsetting, i.e., $\beta_1$ may be from about 1° to about 20°, more desirably from about 5° to about 20°, for example from about 5° to about 15°.

The undulating stent portions 26 may comprise a single wire 25 or wires 25 that have been helically wound to form the stent 24. The wire 25 or wires 25 at the stent ends 12', 14' may be joined by welding, clamping and the like to form an atraumatic end or ends. In other word, the stent 24 of the present invention is desirably free or substantially free of loose wire ends at either or both of the open ends 12', 14'. The undulating stent portions 26 of the present invention are not limited to helically wound wire 25 or wires 25, and such undulating stent portions 26 may be formed by other suitable methods. For example, the stent 24 with the undulating stent portions 26 may be machined from a stock of material, including a tubular stock. Such machining may include, without limitation, laser cutting, chemical etching, electrochemical etching, molding, and the like.

Figure 15:
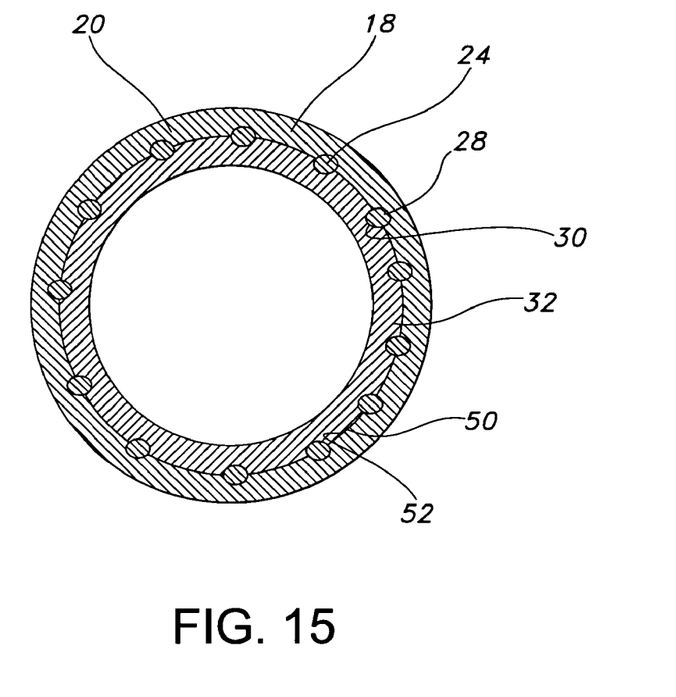
FIG. 15 is a cross-sectional view of the stent-graft of FIG. 2 taken along the 15-15 axis.

FIG. 15 is a cross-sectional view of the stent-graft of FIG. 2 taken along the 15-15 axis. As depicted in FIG. 15, the graft region 20 is secured to exterior surfaces 28 of the stent 24. The second polymeric graft structure 32 may be disposed over the luminal surfaces 30 of the stent 24. Additionally, portions 50 of graft 18 may be securably disposed to portions 52 of the graft 32 through the stent interstices.

Figure 16:
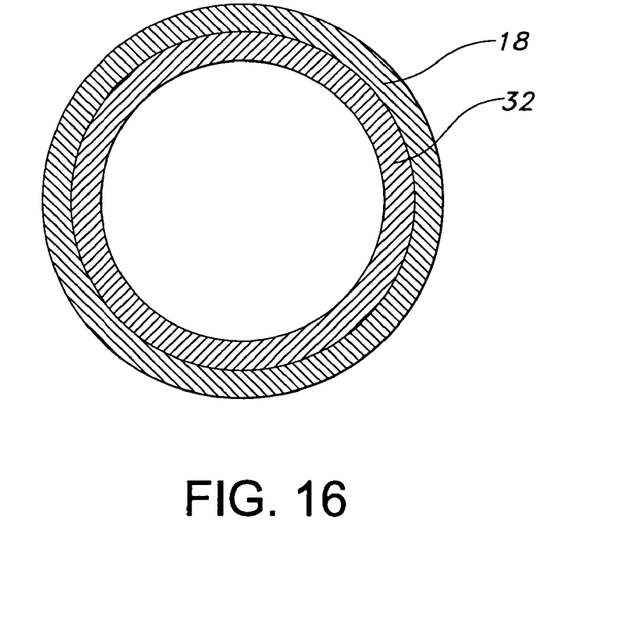
FIG. 16 is a cross-sectional view of the stent-graft of FIG. 2 taken along the 16-16 axis.

As depicted in FIG. 16, which is a cross-sectional view of the stent-graft 10 of FIG. 2 taken along the 16-16 axis, not all portions of the second graft layer 32 need be securably attached to the luminal stent surfaces 28. This is especially true where the peaks 46 of adjacent undulating stent portion 26 are longitudinally offset in a non-nested fashion, for example, being offset by a length $O_1$.

The non-textile, polymeric graft portions 18, 32 of the present invention may be secured to one and the other and/or secured to the stent 24 through any suitable means, including without limitation lamination and/or adhesive bonding. The bonding agent may include various biocompatible, elastomeric bonding agents such as urethanes, styrene/isobutylene/styrene block copolymers (SIBS), silicones, and combinations thereof. Other similar materials are contemplated. Desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent. Details of suitable bonding agents and methods for bonding are further described in U.S. Patent Application Publication Nos. 2003/0017775 A1 and 2004/0182511 A1, the contents of which are incorporated herein by reference.

A method of making the stent-graft 10 of the present invention having increased bending flexibility includes the steps of providing a radially distensible, tubular stent comprising opposed open ends and a stent wall structure having opposed exterior and luminal surfaces; providing a continuous and seamless ePTFE tubular graft having a node and fibril structure securably disposed to one of said stent surfaces, said graft comprising a tubular wall substantially free of slits, apertures and folds, said graft further comprising a first region and a second region; and providing said first region with a different bending flexibility from said second region. The step of providing said first region with a different bending flexibility from said second region may comprise providing at least one circumferential recess at said second region of said graft. The step of providing said first region with a different bending flexibility from said second region may, in addition or in the alternative, comprise axially stretching said first region by a first amount; and axially stretching said second region by a second amount, wherein said first amount being greater than said second amount.

With any embodiment, the stent-graft 10 may be used for a number of purposes including to maintain patency of a body lumen, vessel or conduit, such as in the coronary or peripheral vasculature, esophagus, trachea, bronchi colon, biliary tract, urinary tract, prostate, brain, and the like. The devices of the present invention may also be used to support a weakened body lumen, or to provide a fluid-tight conduit for a body lumen, or support a weakened or kinked device in a lumen, for example adjunctive use. Adjunctive use involved the deployment of a second device, for example stent-graft 10, to a target site having a device, such as a stent, a graft or stent-graft previously positioned thereat. The stent-graft 10 of the present invention may be used to completely or partially overlap the previous device to alleviate a weakening or a kinking of the previous device, i.e., adjunctive deployment or adjunctive use.

Also, the stent-graft 10 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Figure 17:
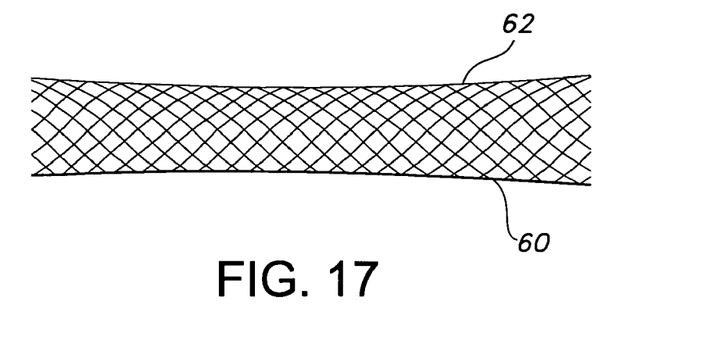
FIG. 17 is a longitudinal view of a wire stent of the present invention.

As described above, various stent types and stent constructions may be employed in the invention as the stent 24 in the stent-graft 10. Non-limiting examples of suitable stent geometries for stent 24 are illustrated in FIGS. 17-21. As shown in FIG. 17, wire stent 60 is a hollow tubular structure formed from wire strand 62 or multiple wire strands. Wire stent 60 may be formed by, for example, braiding or spinning wire strand(s) 62 over a mandrel (not shown). Wire stent 60 is capable of being radially compressed and longitudinally extended for implantation into a bodily lumen. The degree of elongation depends upon the structure and materials of the wire stent 60 and can be quite varied, for example, about 5% to about 200% of the length of wire stent 60. The diameter of wire stent 60 may also become several times smaller as it elongates. Unitary stent structures may be obtained by braiding and/or filament winding stent wires to obtain complex stent geometries, including complex stent geometries, including complex bifurcated stents. Alternatively, stent components of different sizes and/or geometries may be mechanically secured by welding or suturing. Additional details of wire stents of complex geometry are described in U.S. Pat. Nos. 6,325,822 and 6,585,758, the contents of which are incorporated herein by reference.

Figure 18:
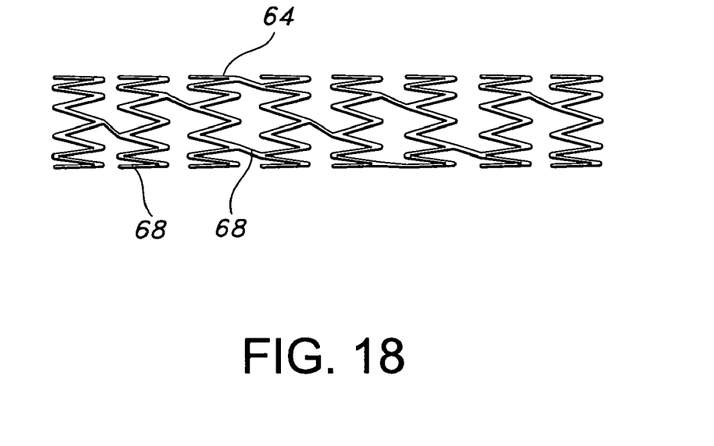
FIG. 18 is a longitudinal view of a zig-zag stent of the present invention.

A zig-zag wire stent 64 is also useful as stent 24. Wire strand 66 is being arranged in what can be described as a multiple of "Z" or "zig-zag" patterns to form a hollow tubular stent. The different zig-zag patterns may optionally be connected by connecting member 68. Further, zig-zag wire stent 64 is not limited to a series of concentric loops as depicted in FIG. 18, but may be suitably formed by helically winding of the "zig-zag" pattern over a mandrel (not shown).

Figure 19:
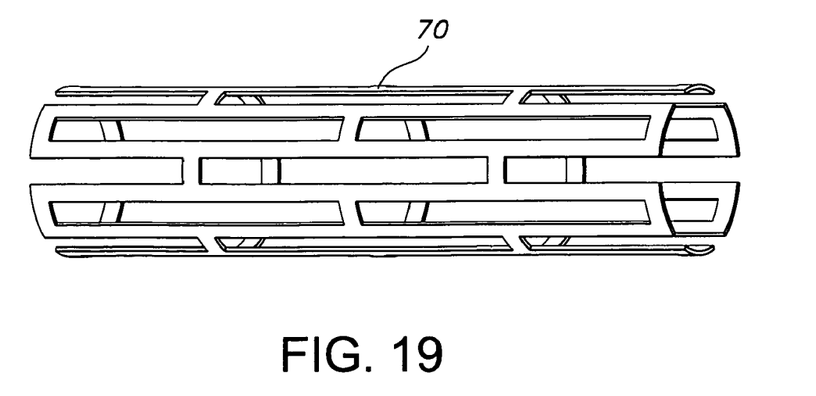
FIG. 19 is a perspective view of slotted stent of the present invention.

A slotted stent 70 is also useful as stent 24. As depicted in FIG. 19, slotted stent 70 is suitably configured for implantation into a bodily lumen (not shown). Upon locating the slotted stent 70 at the desired bodily site, slotted stent 70 is radially expanded and longitudinally contracted for securement at the desired site.

Figure 20:
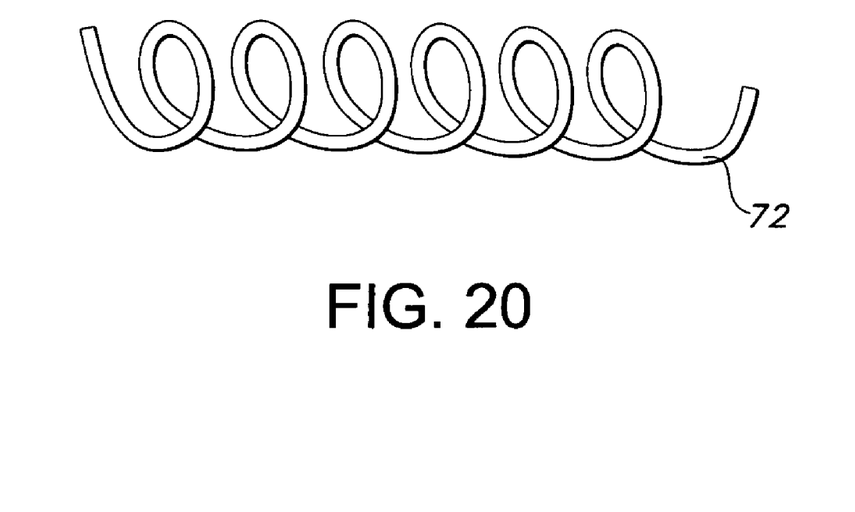
FIG. 20 is a perspective view of a helical coil stent formed of a single wound wire according to the present invention.
Figure 21:
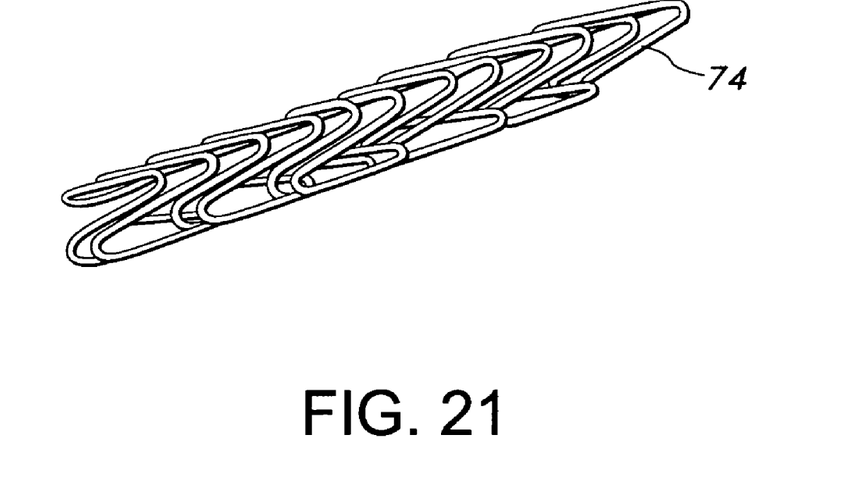
FIG. 21 is a perspective view of a stent having an elongate pre-helically coiled configuration according to the present invention.

Other useful stents capable of radial expansion are depicted in FIGS. 19 and 20. As depicted in FIG. 20, stent 72 is a helical coil which is capable of achieving a radially expanded state (not shown). Stent 74, as depicted in FIG. 21, has an elongate pre-helically coiled configuration as shown by the waves of non-overlapping undulating windings. These helically coiled or pre-helically stents, commonly referred to as nested stents, are also useful with the practice of the present invention.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An endoprosthesis comprising:
    a radially distensible, tubular stent comprising opposed open ends, a stent wall structure having opposed exterior and luminal surfaces and an undulating wire helically wound into a plurality of circumferential adjacent windings to define said stent wall structure; and
    a continuous and seamless ePTFE tubular covering having a node and fibril structure securably disposed to at least one of said stent surfaces, said covering comprising a tubular wall extending between said opposed ends of said tubular stent, said tubular wall having a luminal surface that extends therealong, said tubular wall consisting of first regions and second regions, wherein said first regions are securably attached to said circumferential windings of said undulating wire and are free of circumferential recesses, said fibril structure at said first regions is more circumferentially oriented than said fibril structure at said second regions;
    wherein said second regions of said ePTFE covering are disposed between adjacent windings of said circumferential windings of said undulating wire; and
    wherein said second regions of said covering each comprise three longitudinally side-by-side circumferential recesses and have greater bending flexibility than said first regions, said circumferential recesses extending only part way through said tubular wall of said tubular covering and said luminal surface of said tubular covering being free of said recesses.

2. The endoprosthesis of claim 1, wherein said stent further comprises a longitudinal length, wherein said longitudinal length remains substantially constant upon radial expansion or radial contraction of said stent.

3. The endoprosthesis of claim 1, wherein said stent is a self-expanding stent, a balloon-expandable stent or combinations thereof.

4. The endoprosthesis of claim 1, wherein said stent comprises a biocompatible material selected from the group consisting of metallic materials, polymeric materials, bioabsorbable materials, biodegradable materials, and combination thereof.

5. The endoprosthesis of claim 1, wherein said stent comprises a plurality of undulating stent segments.

6. The endoprosthesis of claim 1, wherein said second regions preferentially deform when subjected to a bending stress as compared to said first regions.

7. The endoprosthesis of claim 1, wherein the fibril structure at said first regions was formed by axially stretching said first regions by a first amount and the fibril structure at said second regions was formed by axially stretching the second regions by a second amount, said first amount being greater than said second amount.

8. The endoprosthesis of claim 7, wherein said first amount of axial stretching is from about 1,000% to about 2,000% and said second amount of axial stretching is from about 200% to about 800%.

9. The endoprosthesis of claim 8, wherein said second regions preferentially deform when subjected to a bending stress as compared to said first regions.

10. The endoprosthesis of claim 1, further comprising a second ePTFE tubular graft securely disposed to the other of one said stent surfaces.

11. The endoprosthesis of claim 1 wherein said second regions plastically deform at a lower force than said first regions.

12. An implantable prosthesis comprising:
    a tubular stent comprising a plurality of circumferential windings defining a stent wall, said stent wall having opposed exterior and luminal surfaces; and
    a non-textile polymeric tubular graft comprising a continuous tubular wall securably attached to at least one of said stent surfaces, said tubular wall having a luminal surface extending along the length of said tubular graft, said tubular graft having a node and fibril structure and consisting of first regions and second regions, said fibril structure at said first regions being more circumferentially oriented than said fibril structure at said second regions, said second regions each comprising three longitudinally side-by-side circumferential recesses, said circumferential recesses extending only part way through said tubular wall of said tubular graft, said luminal surface of said tubular graft being free of said recesses;
    said first regions being securably attached to said circumferential windings and said second regions being disposed between said circumferential windings, wherein said first regions are free of circumferential recesses and have a different bending flexibility than said second regions.

13. The prosthesis of claim 12, wherein said first regions have a different plastic deformation rate than said second regions.

14. The prosthesis of claim 12 wherein said graft comprises expanded polyetrafluoroethylene.

15. The prosthesis of claim 12, wherein the fibril structure at said first regions was formed by axially stretching said first regions by a first amount and the fibril structure at said second regions was formed by axially stretching said second regions by a second amount, said first amount being greater than said second amount.

16. The prosthesis of claim 15, wherein said first amount of axial stretching is from about 1,000% to about 2,000% and said second amount of axial stretching is from about 200% to about 800%.

17. The prosthesis of claim 15, wherein said second regions preferentially deform when subject to a bending stress as compared to said first regions.

18. The prosthesis of claim 12, wherein said tubular wall is substantially free of folds, crimps and pleats.

19. A method of making a stent-graft comprising:
providing a radially distensible tubular stent having a plurality of adjacent windings, said tubular stent comprising opposed open ends and a stent wall structure having opposed exterior and luminal surfaces;
providing a continuous ePTFE tubular graft extending between said opposed open ends of said stent, said ePTFE tubular graft having a node and fibril structure, said graft securably disposed to one of said stent surfaces, said graft comprising a continuous tubular wall having a luminal surface extending along the length of said tubular graft, said tubular wall consisting of first regions free of circumferential recesses and second regions, each second region comprising three longitudinally side-by-side circumferential recesses, wherein said circumferential recesses extend only part way through said tubular wall of said tubular graft, said luminal surface of said tubular wall being free of said recesses, said fibril structure at said first regions is more circumferentially oriented than said fibril structure at said second regions;
securably attaching said windings to said first regions;
positioning said second regions between adjacent windings; and
providing said first regions with a different bending flexibility from said second regions.

20. The method of claim 19, wherein the step of providing said first regions with a different bending flexibility from said second regions comprises: axially stretching said first regions by a first amount; and axially stretching said second regions by a second amount, wherein said first amount being greater than said second amount.

21. The method of claim 20, wherein said first amount of axial stretching is from about 1,000% to about 2,000% and said second amount of axially stretching is from about 200% to about 800%.

22. The endoprosthesis of claim 19 wherein said second regions plastically deform at a lower force than said first regions.

23. A method of supporting a stent-graft previously deployed within a bodily lumen, comprising:
providing:
an endoprosthesis comprising a radially distensible, tubular stent having a plurality of adjacent windings, said tubular stent comprising opposed open ends and a stent wall structure having opposed external and luminal surfaces, and
a continuous and seamless ePTFE tubular covering extending between said opposed open ends of said stent, said ePTFE tubular covering having a node and fibril structure securably disposed to at least one of said stent surfaces, said covering comprising a tubular wall having a luminal surface extending along the length of said tubular covering, said tubular wall consisting of first regions free of circumferential recesses and second regions, said fibril structure at said first regions is more circumferentially oriented than said fibril structure at said second regions, each second region comprising three longitudinally side-by-side circumferential recesses, said first regions having a different bending flexibility from said second regions, said circumferential recesses extend only part way through said tubular wall of said covering, said luminal surface of said tubular covering being free of said recesses, wherein said first regions are securably attached to said adjacent windings and said second regions are positioned between said adjacent windings;
deploying the endoprosthesis within the previously deployed stent-graft; and
expanding the endoprosthesis to support the previously deployed stent-graft.

24. A prosthesis comprising:
a stent comprising an undulating wire wound into a plurality of circumferential windings defining opposed exterior and luminal surfaces of said stent;
a continuous and seamless ePTFE tubular covering having a node and fibril structure securably disposed to at least one of said stent surfaces, said covering comprising a tubular wall extending between the ends of said stent, said covering consisting of first regions and second regions, wherein said fibril structure at said first regions is more circumferentially oriented than said fibril structure at said second regions;
said first regions being free of indentations, said first regions securably attached to said circumferential windings;
said second regions of said ePTFE covering being disposed between adjacent windings of said circumferential windings of said undulating wire;
wherein each of said second regions of said covering comprises three longitudinally side-by-side indentations, said indentations not extending all the way through said covering, said second regions having a greater bending flexibility than said first regions.

25. The endoprosthesis of claim 24 wherein said second regions plastically deform at a lower force than said first regions.

26. An endoprosthesis comprising:
a radially distensible, tubular stent comprising opposed open ends, a stent wall structure having opposed exterior and luminal surfaces and an undulating wire helically wound into a plurality of circumferential adjacent windings to define said stent wall structure; and
a continuous and seamless ePTFE tubular covering having a node and fibril structure securably disposed to at least one of said stent surfaces, said covering comprising a tubular wall having a luminal surface extending along the length of said tubular covering, said tubular wall comprising a first region and second region, said fibril structure at said first regions is more circumferentially oriented than the fibril structure at said second regions, wherein said first region is securably attached to at least one of said circumferential windings of said undulating wire and is free of recesses which extend substantially along a circumferential axis;
wherein said second region of said ePTFE covering is disposed between at least two adjacent windings of said circumferential windings of said undulating wire; and wherein said second region of said covering comprises three circumferential recesses and has a greater bending flexibility than said first region, said circumferential recesses extending only part way through said tubular wall of said tubular covering, said luminal surface of said tubular covering being free of any of said recesses.

27. The endoprosthesis of claim 26 further comprising an anti-inflammatory agent.

28. The endoprosthesis of claim 27, wherein the anti-inflammatory agent consists of sulfasalazine.

* * * * *